(12) United States Patent
Cho et al.

(10) Patent No.: US 7,850,872 B2
(45) Date of Patent: Dec. 14, 2010

(54) COMPOUND FOR MOLECULAR ELECTRONIC DEVICE

(75) Inventors: Gyou-Jin Cho, Suncheon-Si (KR);
Jeong-Ju Kim, Suncheon-Si (KR);
Eun-Jung Choi, Suncheon-Si (KR);
Nam-Young Kim, Gwangju-Si (KR);
Chan-Seok Park, Hwaseong-Si (KR);
Hoe-Taek Yang, Hwaseong-Si (KR)

(73) Assignee: Dongjin Semichem Co., Ltd., Incheon (KR)

( * ) Notice: Subject to any disclaimer, the term of this patent is extended or adjusted under 35 U.S.C. 154(b) by 264 days.

(21) Appl. No.: 11/905,178

(22) Filed: Sep. 27, 2007

(65) Prior Publication Data

US 2008/0087887 A1 Apr. 17, 2008

(30) Foreign Application Priority Data

Sep. 28, 2006 (KR) ...................... 10-2006-0095010

(51) Int. Cl.
*H01B 1/12* (2006.01)
(52) U.S. Cl. ................. 252/500; 257/40; 257/E51.001; 438/99; 528/38
(58) Field of Classification Search ................. 252/500; 257/40, E51.001, E51; 438/99; 528/38
See application file for complete search history.

(56) References Cited

U.S. PATENT DOCUMENTS

| | | | | |
|---|---|---|---|---|
| 6,825,060 | B1* | 11/2004 | Lyons et al. ................... | 438/82 |
| 7,034,100 | B2* | 4/2006 | Han ............................ | 528/210 |
| 2004/0115558 | A1* | 6/2004 | Yang et al. ................. | 430/270.1 |
| 2005/0255405 | A1* | 11/2005 | Kim et al. ................. | 430/270.1 |
| 2006/0011895 | A1* | 1/2006 | Chung et al. ................. | 252/500 |
| 2006/0063858 | A1* | 3/2006 | Kang et al. .................. | 523/160 |
| 2006/0115767 | A1* | 6/2006 | Shin et al. ................. | 430/270.1 |
| 2006/0141392 | A1* | 6/2006 | Yoon et al. ................ | 430/270.1 |
| 2006/0180796 | A1* | 8/2006 | Adachi et al. ................ | 252/500 |
| 2006/0180797 | A1* | 8/2006 | Merker et al. ................ | 252/500 |
| 2006/0180810 | A1* | 8/2006 | Lee et al. ....................... | 257/40 |
| 2008/0051483 | A1* | 2/2008 | Cho et al. ...................... | 522/62 |
| 2010/0012929 | A1* | 1/2010 | Nakano et al. ................ | 257/40 |

OTHER PUBLICATIONS

Reg. No. 1019647-24-5, May 6, 2005.*
"Cyclobutadiene", Wikipedia (Apr. 19, 2009), pp. 1 and 2.*
Facchetti et al., Advanced Materials, vol. 17, pp. 1705-1725, Gate Dielectrics for Organic Field-Effect Transistors: New Opportunities for Organic Electronics, 2005).
Fujita et al., Acta Cryst., vol. 51, Part 11, p. 2265-2269, Two Cobaltacyclopentadiene Complexes and One Cyclobutadiene Complex, (Nov. 1995).
Ramakrishna et al., Organometallics, vol. 21, No. 26, Cp2Zr(η2-benzocyclobutadiene)(PMe3), a Rare η2-Cyclobutadiene Complex (Dec. 2002), pp. 5685-5687.
Sirringhaus et al., Science, vol. 280, pp. 1741-1744, Integrated Optoelectronic Devices Based on Conjugated Polymers (Jun. 1998).
Waybright et al., Organometallics, vol. 19, pp. 368-370, Synthesis and Self-Assembly of an Oligonucleotide-Modified Cyclobutadiene Complex (2000).

* cited by examiner

*Primary Examiner*—Douglas Mc Ginty
(74) *Attorney, Agent, or Firm*—Birch, Stewart, Kolasch & Birch, LLP

(57) ABSTRACT

Disclosed are a compound which works as electronic materials such as a molecular memory, a molecular switch, a molecular rectifier, a molecular wire, and so on, and a molecular electronic device including the same. The compound for molecular electronic device has the structure of following Formula 1, $(M)_n\text{-}R\text{-}(M)_n$            <Formula 1> wherein, R is a single molecule having an electrical conductivity, M is independently a repeating unit constituting a polymer having an electrical conductivity, and n is independently an integer ranging from 100 to 500.

11 Claims, 5 Drawing Sheets

[FIG. 1]
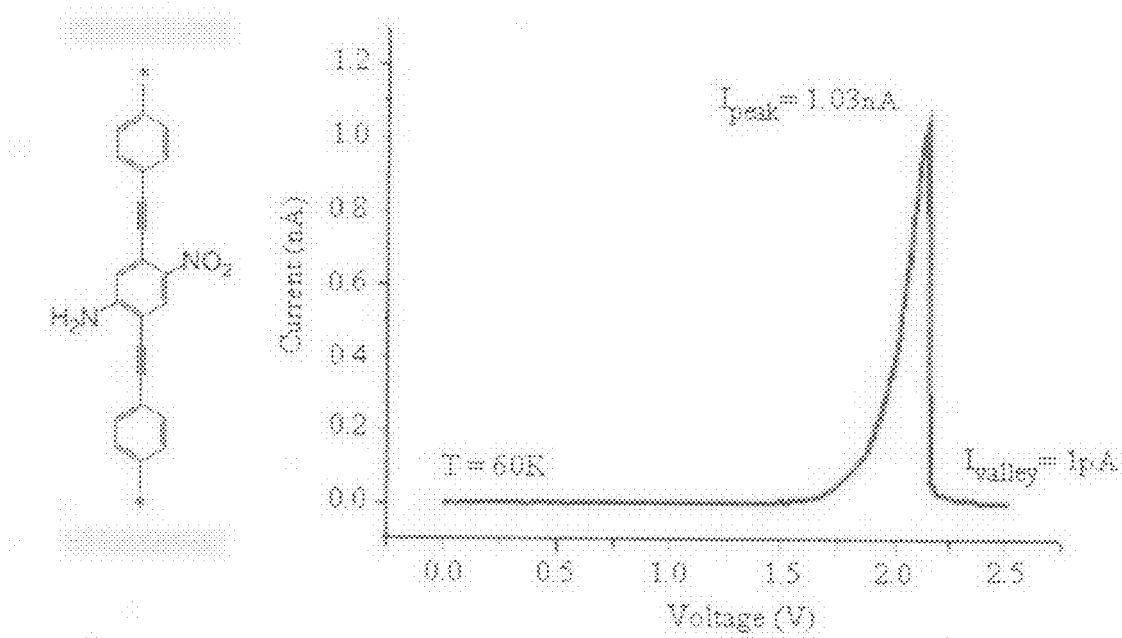

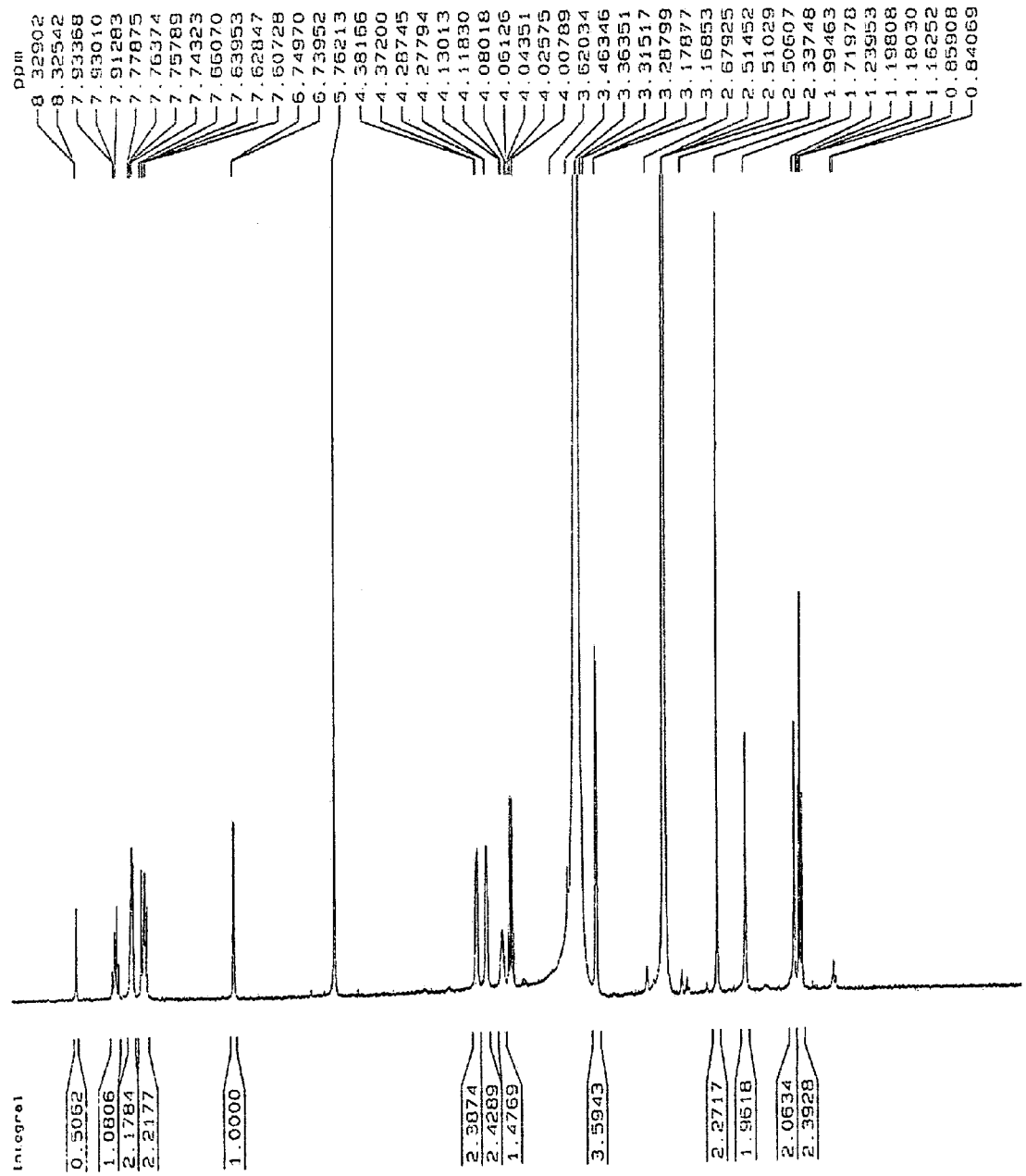
[FIG. 2]

[FIG. 3]
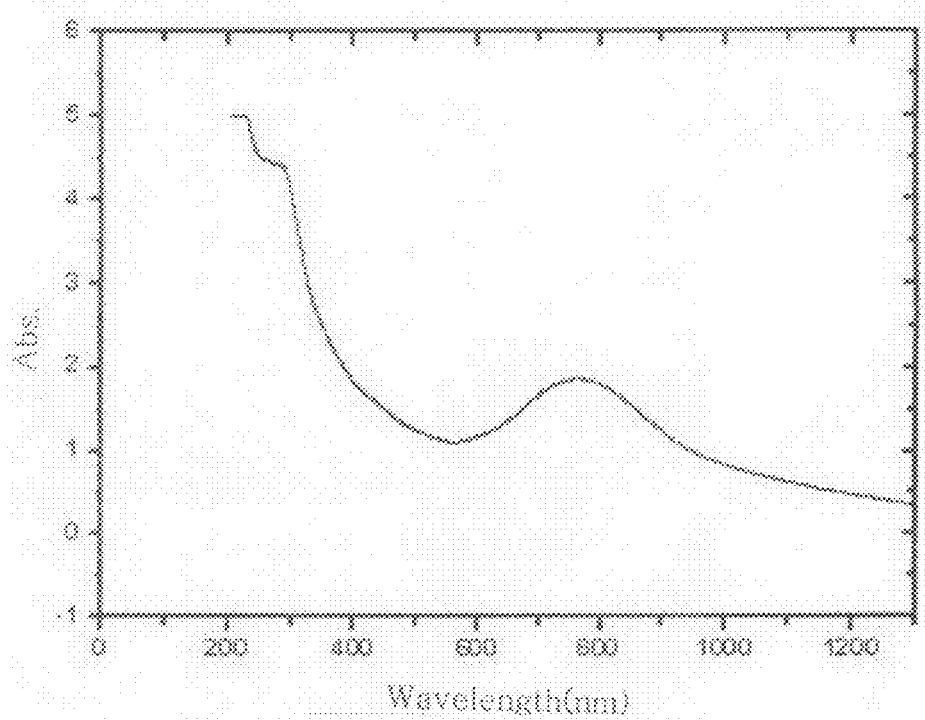
[FIG. 4]
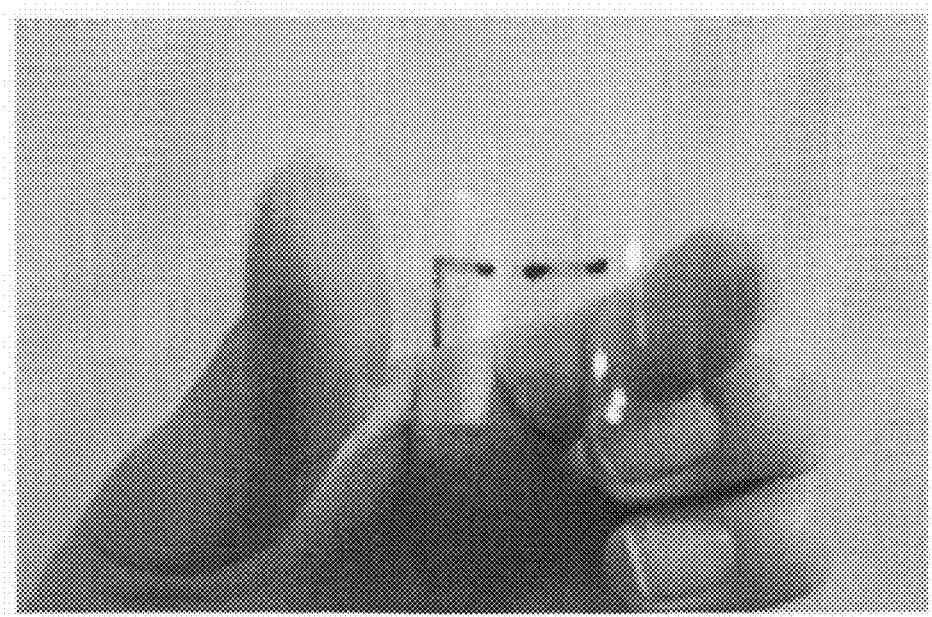

[FIG. 5]
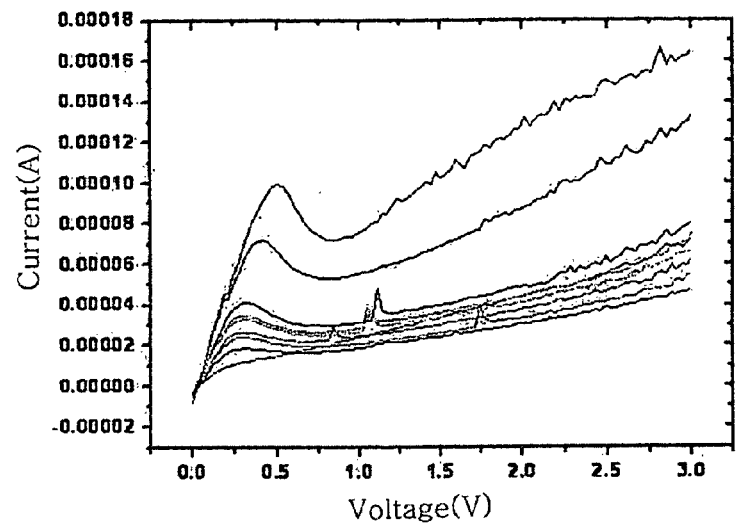
[FIG. 6]
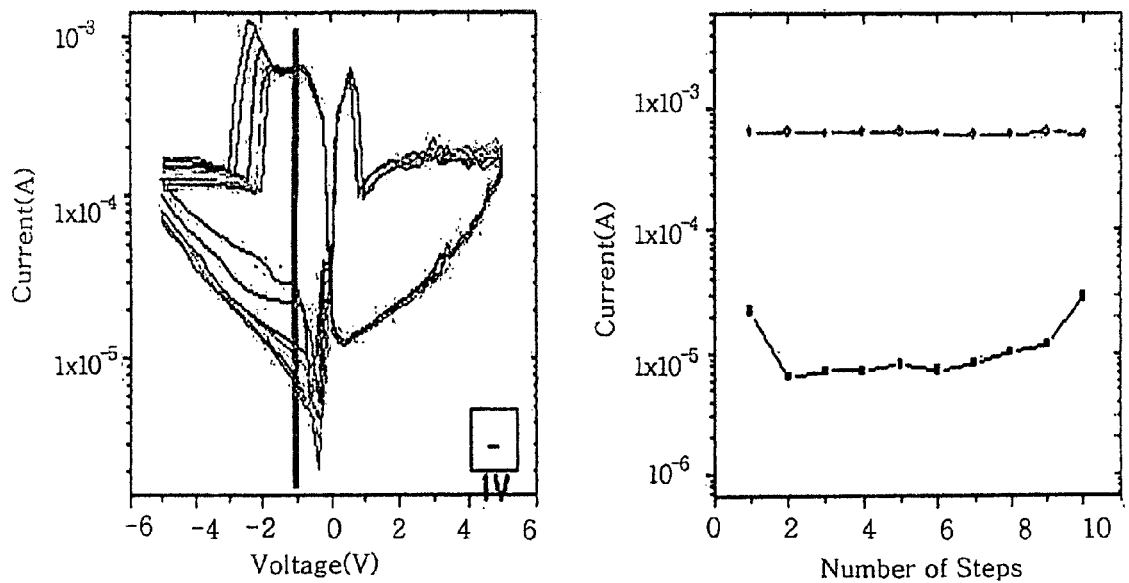

[FIG. 7]
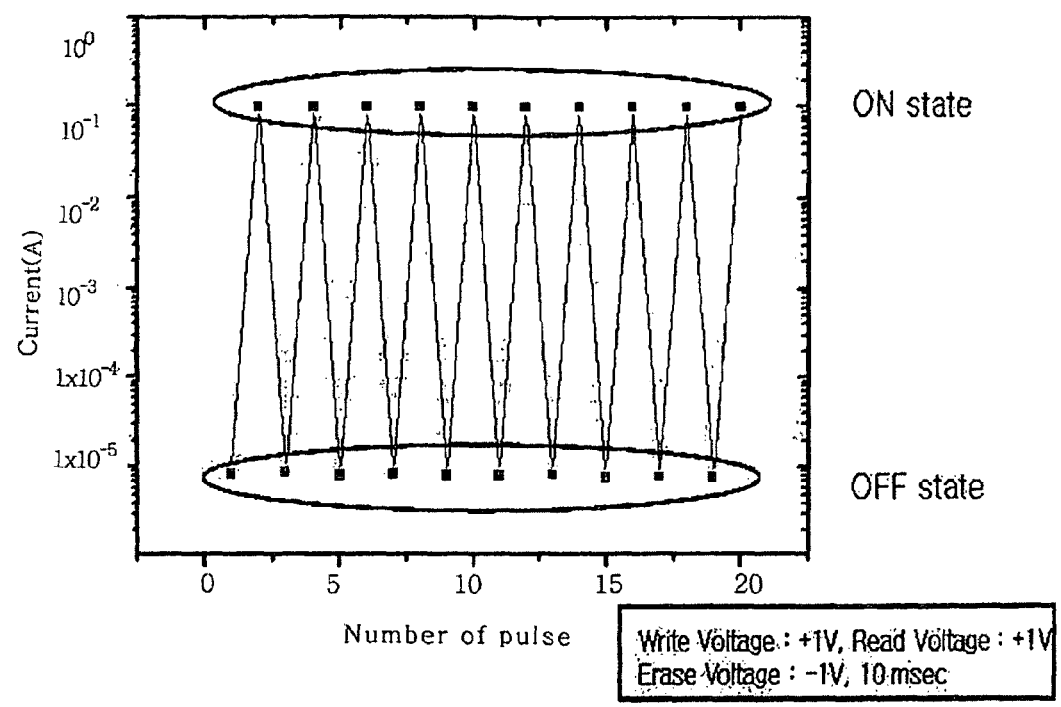

COMPOUND FOR MOLECULAR ELECTRONIC DEVICE

This application claims the priority benefit of Korean Patent Application No. 10-2006-0095010 filed on Sep. 28, 2006. All disclosure of the Korean Patent application is incorporated herein by reference.

FIELD OF THE INVENTION

This invention relates to a compound for molecular electronic devices and a molecular electronic device including the same. More specifically, this invention relates to a compound which works as electronic materials such as a molecular memory, a molecular switch, a molecular rectifier, a molecular wire, and so on, and a molecular electronic device including the same.

BACKGROUNDS OF THE INVENTION

Generally, an organic compound based electronic device represents an electronic device which can process or transform electronic, magnetic, or optical signals with organic molecules. Commercial examples of the organic compound based electronic device include a liquid crystal display device, an organic light emitting diode, and so on. In a narrow sense, the organic compound based electronic device also represents an electronic device having a molecular size, for example, a molecular memory, a molecular switch, a molecular rectifier, a molecular wire, and so on. Because most of molecules have the size of several nanometers, the organic compound based electronic device is called as "molecular nano-electronic device".

The molecular electronic device has advantages in its size, function, mass production, and so on, compared with a conventional semiconductor device. Specifically, the size of a molecular electronic device is much smaller than that of a silicon device. Thus, it is possible to produce an electronic device of large scale integration with the molecules. In addition, a molecule may have various functions. For example, in a conventional silicon technology, both of transistors and capacities are necessary to produce a memory. However, in a molecular electronic device, a molecule can work as a memory. Also, by using the molecule's self-assembling properties, tens of millions or hundreds of millions of devices can be simultaneously assembled in a solution state, and accordingly the cost of equipment and facilities for manufacturing the electronic device can be innovatively decreased. Considering the cost for increasing the integration degree of a semiconductor, there should be a limitation in increasing the integration degree of a semiconductor. For example, it is known that Intel Corporation spent 12 thousand dollars in building a semiconductor manufacturing factory on 1968, but on 2000, spent almost 12 million dollars in building a factory having the same capacities. That is, the cost will increase by a geometric progression as the integration degree increases. In other words, because of costs of equipment and facilities rather than lacks of the integration technology, there is a limitation in increasing the integration degree of a semiconductor. After all, in 20 to 30 years from now, the Moore's Law may not work. To solve these problems, a study on a molecular electronic device is necessary.

Aviram and Ratner proposed a theoretical molecular diode in 1974, in which a molecule was interposed between two metal electrodes. Reed of Yale University, Tour of Rice University, and so on proposed a sandwich structure device showing a Negative Differential Resistance (NDR) effect, by locating nano-pore membrane having electron donor and electron acceptor functional groups between two metal electrodes. FIG. 1 is a structure of a conventional molecular electronic device showing Negative Differential Resistance (NDR) characteristics and a graph showing the current (nA)–voltage (V) characteristics thereof. As shown in FIG. 1, a molecule is interposed between a pair of electrodes by covalent bonding to form a molecular electronic device. The device works as a diode which transmits currents at a predetermined voltage. However, in the conventional molecular electronic device, a single molecular layer having the average size of less than 10 nm must be positioned between metal electrodes. Thus, there are disadvantages that the production cost is high and an electronic short between the electrodes may easily occur. The electronic short deteriorates the uniformity of the electronic device, and makes it difficult to commercially use the molecular electronic device.

SUMMARY OF THE INVENTION

Therefore, it is an object of the present invention to provide a compound for molecular electronic devices which can decrease an electronic short between metal electrodes, and a molecular electronic device including the same.

It is another object of the present invention to provide a compound for molecular electronic devices which can produce a molecular electronic device economically and efficiently, and a molecular electronic device including the same It is still another object of the present invention to provide a compound for molecular electronic devices which has solubility for forming an ink, a molecular electronic device produced by a printing method using the ink, and a method for manufacturing the molecular electronic device.

To accomplish these objects, the present invention provide a compound for molecular electronic devices having the structure of the following Formula 1, $$(M)_n\text{-}R\text{-}(M)_n \qquad \text{[Formula 1]}$$

in Formula 1, R is a single molecule having an electrical conductivity, M is independently a repeating unit constituting a polymer having an electrical conductivity, and n is independently an integer ranging from 100 to 500.

The present invention also provides a molecular electronic device including the compound having the structure of Formula 1.

The present invention also provides a method for producing a molecular electronic device comprising the steps of; patterning a lower electrode on a substrate; coating an ink, in which the compound having the structure of Formula 1 is dissolved in a solvent, on the lower electrode and then removing the solvent; and forming an upper electrode on the compound having the structure of Formula 1.

BRIEF DESCRIPTION OF THE DRAWINGS

FIG. 1 is a structure of a conventional molecular electronic device showing Negative Differential Resistance (NDR) characteristics and a graph showing current (nA) and voltage (V) characteristics thereof.

FIG. 2 is a NMR spectrum of a monomer for molecular electronic devices produced in Example 1-1 of the present invention.

FIG. 3 is a graph showing absorbance of a compound for molecular electronic devices produced in Example 2-1 of the present invention, measured with UV-Near IR.

FIG. 4 is a photograph of a molecular electronic device produced in Example 3-1 of the present invention.

FIG. 5 is a graph showing V (voltage) vs I (current) characteristics of a molecular electronic device produced in Example 3-1 of the present invention.

FIG. 6 is a graph showing a hysteresis characteristic of a molecular electronic device produced in Example 3-1 of the present invention.

FIG. 7 is a graph showing read (+1V)/erase (−1V) stability test results of a molecular electronic device produced in Example 3-2 of the present invention.

DETAILED DESCRIPTION OF THE INVENTION

A more complete appreciation of the invention, and many of the attendant advantages thereof, will be better appreciated by reference to the following detailed description.

A compound for molecular electronic devices according to the present invention has the structure of the following Formula 1, in which a single molecule having an electrical conductivity is chemically bonded between polymers having electrical conductivities.

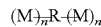   [Formula 1]

In Formula 1, R is a single molecule having an electrical conductivity, preferably a conjugated single molecule having an electron donor group and an electron acceptor group, and more preferably a single molecule having a memory function. M is independently a repeating unit constituting a polymer having an electrical conductivity, and n is independently an integer ranging from 100 to 500.

As the single molecule having an electrical conductivity (R), any single molecule useful in forming a molecular electronic device can be used. Preferable single molecule can be represented by the following Formula 2.

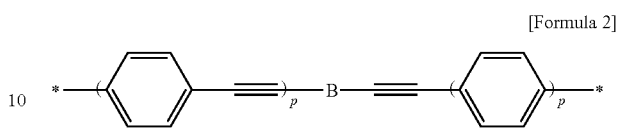   [Formula 2]

In Formula 2, p is independently an integer from 0 to 10, preferably from 1 to 3. B is a substituted or non-substituted $C_4$~$C_{30}$ (4 to 30 carbon atoms) ring structure compound in which a double bond and a single bond are alternately repeated, preferably, is a $C_4$~$C_{10}$ aryl or heteroaryl group, and more preferably, is a phenyl group or a pyridine group substituted with an amino group or a nitro group. Exemplary substituent which can be substituted to B includes an amino group, a nitro group, alkyl group of 1 to 5 carbon atoms, an aryl or heteroaryl group of 4 to 6 carbon atoms, and so on. When the substituent has a structure in which a double bond and a single bond are alternately repeated, the B can be connected with the alkyne group of Formula 2. Examples of the single molecule having an electrical conductivity (R) of Formula 2 include

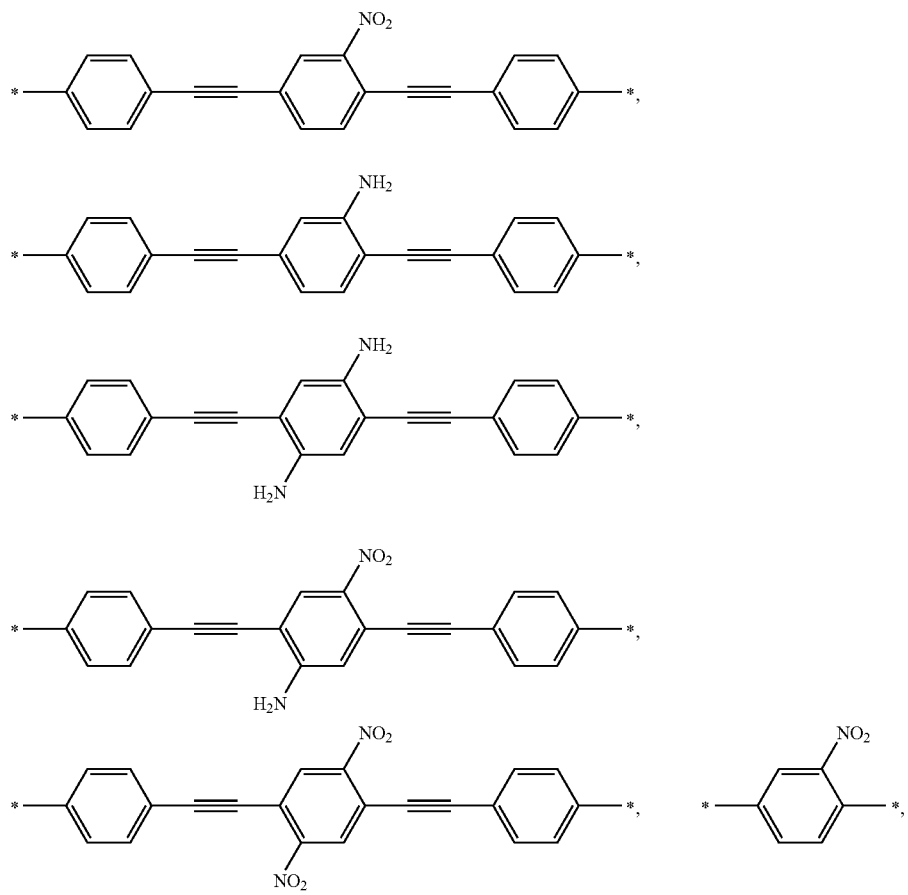

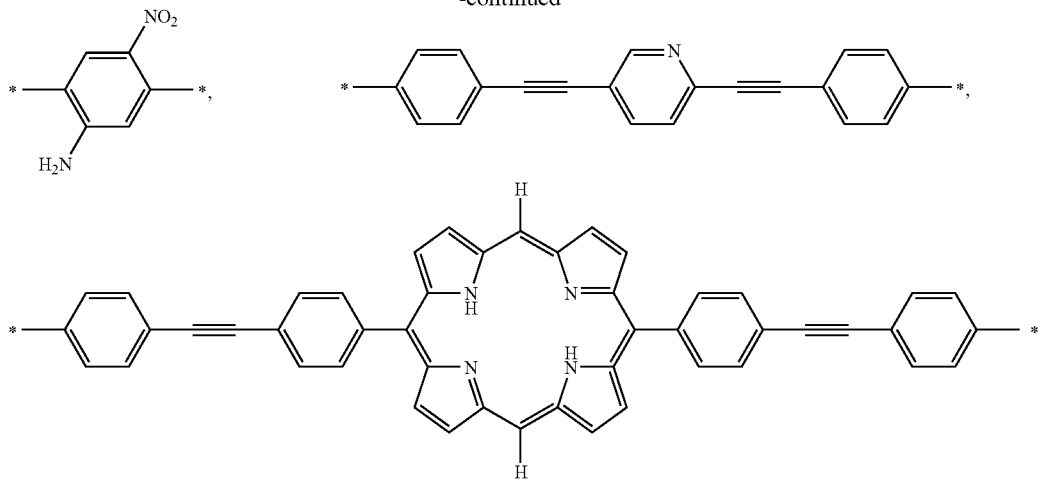

, and so on, wherein * represents a connecting part. When the B has a ring structure such as

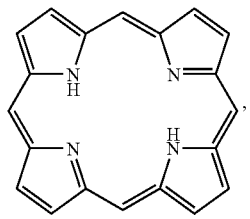

, metal such as Cu, Au, Ag, Mg, Cd, and so on may be inserted into inside of the ring structure to change the electronic state of the ring structure. When a voltage is applied on both sides of the single molecule (R), the single molecule blocks or transits (passes) currents according to the intensity of the applied voltage, or saves electric signals according to the intensity of the applied voltage. That is, the single molecule (R) works as a molecular electronic device, for example, a molecular memory, a molecular switch, a molecular rectifier, a molecular wire, and so on.

In the formula 1, the M is a repeating unit constituting a polymer having an electrical conductivity, and for example, is

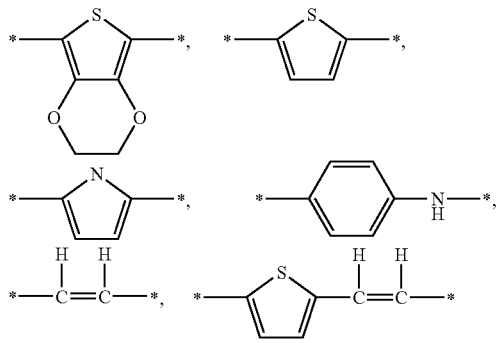

, and so on. The n is a degree of polymerization of the repeating unit, and is an integer ranging from 100 to 500, preferably from 200 to 400. If the degree of polymerization is less than 100, the electrical conductivity decreases, and if more than 500, characteristics of the single molecule (R) are weakened. The polymer having an electrical conductivity $((M)_n)$ works as an electrode for applying voltages by being positioned at both sides of the single molecule (R), and make the single molecule (R) to be uniformly positioned between a pair of electrodes without an electrical short. Because the polymer having an electrical conductivity $((M)_n)$ has a property of being easily dissolved in a solvent, the compound for molecular electronic devices according to the present invention can be produced in the form of an ink, and accordingly the single molecule (R) can be easily located on a desired position by a conventional coating method.

As shown in the following Examples, the compound for molecular electronic devices according to the present invention can be produced by chemically bonding the monomers (M) for forming the polymer $((M)_n)$ to both sides of the single molecule (R), and then mixing the produced compound (M-R-M) and the monomer (M) to produce a mixture, and polymerizing the mixture.

Hereinafter, a method for producing a molecular electronic device according to the present invention will be described. First, a lower electrode is patterned on a substrate, for example, on a flexible plastic substrate, by a printing method, a deposit method, or so on. The electrode can be made of gold; silver, copper, nickel, aluminum, and so on. Then, an ink, in which the compound for molecular electronic devices of the present invention is dissolved in a solvent, is coated, for example, printed on the lower electrode, and then the solvent are removed, for example, by an evaporation method. Then, an upper electrode is formed on the compound having the structure of Formula 1, for example, by deposition. Accordingly, the molecular electronic device of the present invention includes the compound of Formula 1; and a pair of opposing electrodes on which the polymer parts of the compound of Formula 1 are respectively coated. Also, the molecular electronic device can be used as, for example, a molecular memory, a molecular switch, a molecular rectifier, a molecular wire, and so on. On occasion demands, without using the electrodes, the molecular electronic device can be produced by simply printing the ink on a region to which a voltage is applied, and by removing the solvent from the printed ink. In this case, the polymer parts $((M)_n)$ works as the electrodes.

The solvent for dissolving the compound for molecular electronic devices of the present invention includes water, organic solvent, and so on. Exemplary organic solvent includes dimethylformamide (DMF), chloroform (CHCl$_3$), isopropylalcohol, dimethylsulfoxide (DMSO), and so on. The concentration of the compound for molecular electronic devices in the ink is preferably 1 to 10 weight %. If the concentration of the compound is too low, the compound may be insufficiently coated. If the concentration of the compound is too high, it is difficult to carry out the uniform printing or coating.

Hereinafter, the preferable examples are provided for better understanding of the present invention. However, the present invention is not limited to the following examples.

Example 1-1

Preparation of Monomer

A. Synthesis of 4-trimethylsilylethynylaniline

As shown in the following Reaction 1, 300 mg (1.37 mmol) of 4-iodoaniline was melted in 5 mL of trimethylamine, and 0.20 mL (1.46 mmol, 1.07 eq) of trimethylsilylacetylene, 4 mg (0.0068 mmol, 0.5 mol %) of dichlorobis-(triphenylphosphine)palladium(II), and 2 mg (0.013 mmol, 1 mol %) of copper iodide were added thereto, and then the reaction solution was stirred under nitrogen atmosphere for 12 hours. Next, the reaction solution was filtered with ether, and was extracted with 10 mL of 2M ammonium chloride aqueous solution 2 times and with 1M sodium chloride aqueous solution 1 time. The organic solvent layer was dehydrated with magnesium sulfate, filtered, and then distilled under reduced pressure. The compound distilled under reduced pressure was purified with a column chromatography (mobile phase volume ratio; ethylacetate:n-hexane=1:4) to obtain 246 mg of 4-trimethylsilylethynylaniline with the yield of 98%. NMR data of the obtained compound is as follows. [$^1$H NMR (400 MHz, CDCl$_3$): δ 0.24-0.27 (m, 9H), 3.81 (s, 2H), 6.58 (d, 2H), 7.29 (d, 2H)].

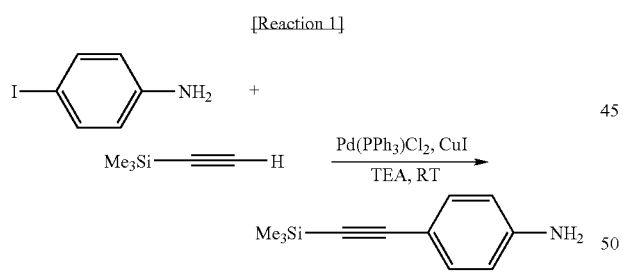

[Reaction 1]

B. Synthesis of 4-trimethylsilylethynyl iodobenzene

As shown in the following Reaction 2, 250 mg (1.32 mmol) of 4-trimethylsilylethynylaniline obtained in A of Example 1-1 was melted in 3 mL of hydrochloric acid at the temperature of 0° C., and 94 mg (1.37 mmol, 1.04 eq) of sodium nitrite was added thereto, and then the reaction solution was stirred for 1 hour. After completion of stirring, 280 mg (1.69 mmol, 1.28 eq) of potassium iodide was added to the reaction solution, and then the reaction solution was stirred at room temperature for 12 hours. Next, the reaction solution was extracted with ether 2 times and 1 time with 1M sodium chloride aqueous solutions 1 time. The organic solvent layer was dehydrated with magnesium sulfate, filtered, and then distilled under reduced pressure. The compound distilled under reduced pressure was purified with an alumina column chromatography (mobile phase: hexane) to obtain 360 mg of 4-trimethylsilylethynyl iodobenzene with the yield of 92%. NMR data of the obtained compound is as follows. [$^1$H NMR (400 MHz, CDCl$_3$): δ 0.23-0.27 (m, 9H), 7.16 (d, 2H), 7.69 (d, 2H)].

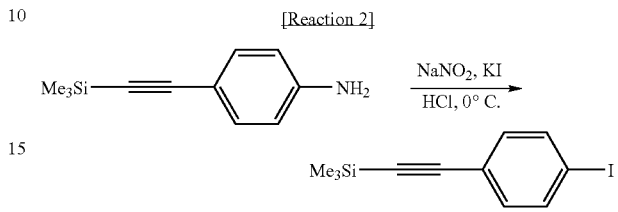

[Reaction 2]

C. Synthesis of [4-(2,3-dihydro-thieno[3,4-b][1,4] dioxin-5-yl)-phenylethynyl]-trimethyl-silane As shown in the following Reaction 3, 580 mg (4.08 mmol) of 3.4-ethylenedioxythiophene was melted in 10 mL of tetrahydrofuran under nitrogen atmosphere at the temperature of −78° C., and 2.45 mL (6.12 mmol, 1.5 eq) of n-butyllithium was added thereto, and then the reaction solution was stirred for 1 hour. After completion of stirring, 1.37 g (6.12 mmol, 1.5 eq) of zinc bromide was again added to the reaction solution at the temperature of 0° C., and then the reaction solution was stirred for 1 hour. Next, 1.22 g (4.08 mmol, 1 eq) of 4-trimethylsilylethynyl iodobenzene and 110 mg (0.16 mmol, 0.04 eq) of dichlorobis-(triphenylphosphine)palladium(II) were added to the reaction solution, and then the reaction solution was stirred for 12 hours at room temperature. After solvents of the reaction solution were removed by distillation under reduced pressure, the compound distilled under reduced pressure was purified with an alumina column chromatography (mobile phase volume ratio: methylene chloride:n-hexane=2:3) to obtain 740 mg of [4-(2,3-Dihydro-thieno[3,4-b][1,4]dioxin-5-yl)-phenylethynyl]-trimethyl-silane with the yield of 58%. NMR data of the obtained compound is as follows. [$^1$H NMR (400 MHz, CDCl$_3$): δ 0.25 (s, 9H), 4.23-4.24 (m, 2H), 4.30-4.32 (m, 2H), 6.32 (s, 1H), 7.44 (d, 2H), 7.64 (d, 2H)].

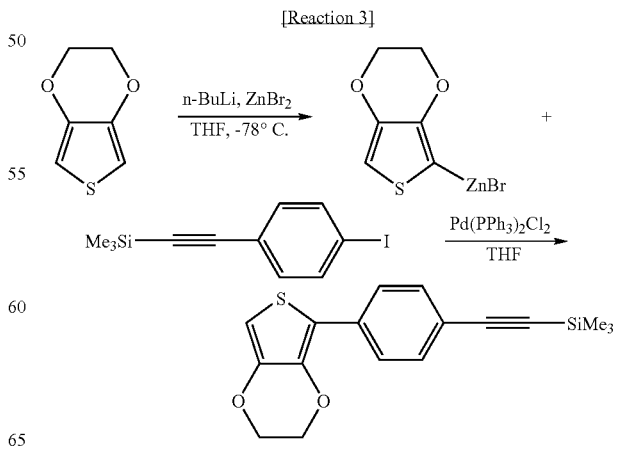

[Reaction 3]

D. Synthesis of 5-(4-Ethynyl-phenyl)-2,3-dihydro-thieno[3,4-b][1,4]dioxine

As shown in the following Reaction 4, 200 mg (0.63 mmol) of [4-(2,3-Dihydro-thieno[3,4-b][1,4]dioxin-5-yl)-phenyl-ethynyl]-trimethyl-silane obtained in C of Example 1-1 was melted in 5 mL of methyl alcohol, and 170 mg (1.27 mmol, 2 eq) of calcium carbonate was added thereto, and then the reaction product was stirred for 12 hours. Next, the reaction solution was extracted with 10 mL of methylene chloride 1 time. The organic solvent layer was dehydrated with magnesium sulfate, filtered, and then distilled under reduced pressure. The compound distilled under reduced pressure was purified with a column chromatography (mobile phase volume ratio: methylene chloride:n-hexane=2:3) to obtain 140 mg of 5-(4-Ethynyl-phenyl)-2,3-dihydro-thieno[3,4-b][1,4]dioxine with the yield of 93%. NMR data of the obtained compound is as follows. [$^1$H NMR (400 MHz, CDCl$_3$): δ 3.10 (s, 1H), 4.23-4.26 (m, 2H), 4.29-4.32 (m, 2H), 6.33 (s, 1H), 7.46 (d, 2H), 7.67 (d, 2H)].

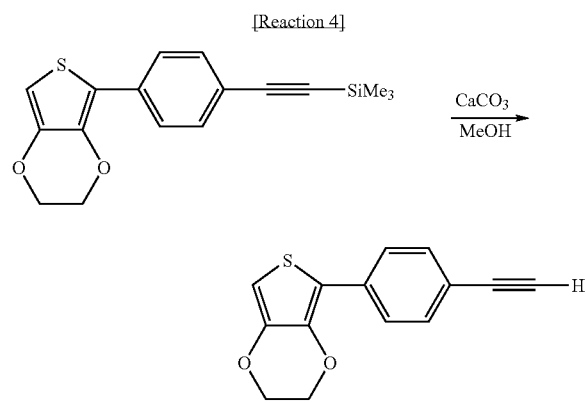

E. Synthesis of Monomer of Compound for Molecular Electronic Devices

As shown in the following Reaction 5, 54 mg (0.19 mmol) of 5-(4-Ethynyl-phenyl)-2,3-dihydro-thieno[3,4-b][1,4]dioxine obtained in D of Example 1-1 was melted in 5 mL of tetrahydrofuran under nitrogen atmosphere, and 110 mg (0.45 mmol, 2.4 eq) of 2,5-dibromonitrobenzene, 2 mg (0.037 mmol, 0.02 eq) of dichlorobis-(triphenylphosphine)palladium(II), 1 mg (0.074 mmol, 0.04 eq) of copper iodide, 2 mg (0.074 mmol, 0.04 eq) of triphenylphosphine, and 0.13 mL (0.74 mmol, 4 eq) of N,N-diisopropylethylamine (Hunig's base) was added thereto, and then the reaction solution was stirred for 72 hours at the temperature of 65° C. Next, the reaction solution was filtered to obtain 74 mg of monomer of a compound for molecular electronic devices with the yield of 68%. NMR data of the obtained compound is as follows. [$^1$H NMR (400 MHz, DMSO-d$_6$): δ 4.28 (d, 4H), 4.37 (d, 4H), 6.74 (d, 2H), 7.61-7.66 (m, 4H), 7.44-7.78 (m, 4H), 7.89-7.95 (m, 2H), 8.32 (s, 1H)].

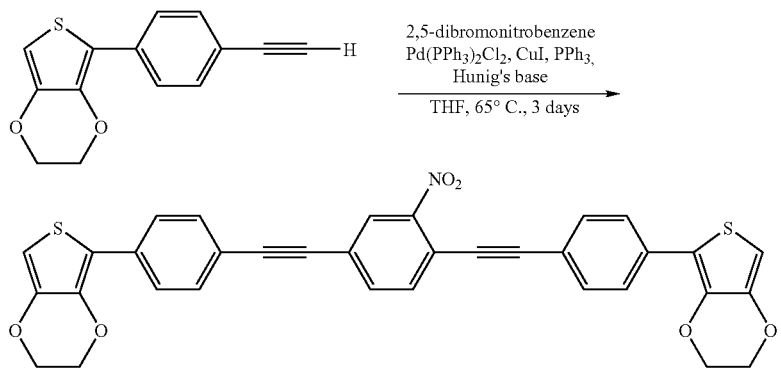

Example 1-2

Preparation of Monomer

A. Synthesis of 4-(trimethylsilylethynyl)benzaldehyde

As shown in the following Reaction 6, 500 mg (2.15 mmol) of 4-iodobenzaldehyde was melted in 2.7 mL of tetrahydrofuran, and 0.45 mL (3.22 mmol, 1.5 eq) of trimethylsilylacetylene, 0.6 mL (3.44 mmol, 1.6 eq) of diisopropylethylamine (DIEA), 7 mg (0.01 mmol, 0.5 mol %) of dichlorobis-(triphenylphosphine)palladium(II), and 3 mg (0.02 mmol, 1 mol %) of copper iodide was added thereto, and then the reaction solution was stirred under nitrogen atmosphere for 12 hours at room temperature. Next, the reaction solution was filtered with ether, and then was extracted with 1M sodium chloride aqueous solution 1 time. The organic solvent layer was dehydrated with magnesium sulfate, filtered, and then distilled under reduced pressure. The compound distilled under reduced pressure was purified with a column chromatography (mobile phase volume ratio; ethylacetate:n-hexane=1:10) to obtain 420 mg of 4-trimethylsilylethynyl benzaldehyde with the yield of 98%. NMR data of the obtained compound is as follows. [$^1$H NMR (400 MHz, CDCl$_3$): δ 9.81 (s, 1H), 7.63 (d, 2H), 7.42 (d, 2H), 0.13 (s, 9H)].

[Reaction 6]

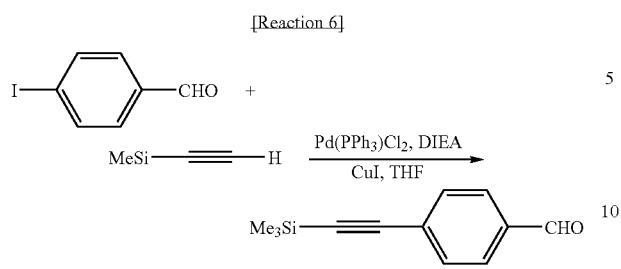

B. Synthesis of 4-Ethynylbenzaldehyde

As shown in the following Reaction 7, 250 mg (1.19 mmol) of 4-trimethylsilylethynyl benzaldehyde obtained in A of Example 1-2 was melted in 10 mL of methylenechloride and 10 mL of methanol at room temperature, and 1.25 g (9.04 mmol, 7.6 eq) of potassium carbonate was added thereto, and then the reaction solution was stirred for 6 hours. Next, the reaction solution was extracted with ether 2 times and with 1M sodium chloride aqueous solution 1 time. The organic solvent layer was dehydrated with magnesium sulfate, filtered, and then distilled under reduced pressure. The compound distilled under reduced pressure was purified with a column chromatography (mobile phase volume ratio; ethylacetate:n-hexane=1:10) to obtain 130 mg of 4-ethynylbenzaldehyde with the yield of 93%. NMR data of the obtained compound is as follows. [$^1$H NMR (400 MHz, CDCl$_3$): δ 10,02 (s, 1H), 7.83 (d, 2H), 7.63 (d, 2H), 3.27 (s, 1H)].

[Reaction 7]

C. Synthesis of 2-(4-bromo-phenyl)-thiophene

As shown in the following Reaction 8, 130 mg (0.6 mmol) of 4-bromophenyl boronic acid was melted in 15 mL of thiophene, and 500 mg (3.22 mmol, 3 eq) of manganese(III) acetate dihydrate was added thereto, and then the reaction solution was refluxed for 1 hour at temperature of 85° C. Next, the reaction solution was filtered with hexane using a funnel charged with silica gel, and dehydrated with magnesium sulfate and distilled under reduced pressure. The compound distilled under reduced pressure was purified with a column chromatography (mobile phase: n-hexane) to obtain 140 mg of 2-(4-bromo-phenyl)-thiophene with a yield of 98%. NMR data of the obtained compound is as follows. [$^1$H NMR (400 MHz, CDCl$_3$): δ 7.50 (m, 4H), 7.25 (d, 2H), 7.07 (t, 1H)].

[Reaction 8]

D. Synthesis of 2-(4-Iodo-phenyl)-thiophene

As shown in the following Reaction 9, 100 mg (0.42 mmol) of 2-(4-bromo-phenyl)-thiophene synthesized in C of Example 1-2 was melted in 5 mL of n-phentanol, and 130 mg (0.84 mmol, 2 eq) of sodium iodide and 0.004 mL (0.042 mmol, 10 mol %) of 1,3-diaminopropane was added thereto, and then the reaction solution was refluxed for 18 hours at temperature of 130° C. Next, the reaction solution was washed with aqueous ammonia, and was dehydrated with magnesium sulfate, filtered, and then distilled under reduced pressure. The compound distilled under reduced pressure was purified with a column chromatography (mobile phase: n-hexane) to obtain 100 mg of 2-(4-iodo-phenyl)-thiophene with the yield of 83.3%. NMR data of the obtained compound is as follows. [$^1$H NMR (400 MHz, CDCl$_3$): δ 7.52 (m, 4H), 7.33 (d, 2H), 7.10 (t, 1H)].

[Reaction 9]

E. Synthesis of 4-thiophenphenylethynylbenzaldehyde

As shown in the following Reaction 10, 150 mg (0.52 mmol) of 2-(4-iodo-phenyl)-thiophene obtained in D of Example 1-2 was melted in 5 mL of water (H$_2$0), and 92 mg (0.78 mmol, 1.5 eq) of 4-ethynylbenzaldehyde obtained in B of Example 1-2, 0.14 mL (0.78 mmol, 1.5 eq) of diisopropylethylamine, 3 mg (0.0026 mmol, 0.5 mol %) of tetrakis (tripheylphosphine)palladium(0), and 1 mg (0.0052 mmol, 1 mol %) of copper iodide was added thereto, and the reaction solution was refluxed for 1 hour at temperature of 90° C. Next, the reaction solution was extracted with ether, and the organic solvent layer was dehydrated with magnesium sulfate, filtered, and then distilled under reduced pressure. The compound distilled under reduced pressure was purified with a column chromatography (mobile phase volume ratio; ethylacetate:n-hexane=1:10) to obtain 130 mg of 4-thiophenphenylethynylbenzaldehyde with the yield of 87%. NMR data of the obtained compound is as follows. [$^1$H NMR (400 MHz, CDCl$_3$): δ 10.01 (s, 1H), 7.86 (d, 2H), 7.68 (d, 2H), 7.62 (d, 2H), 7.56 (d, 2H), 7.37 (dd, 1H), 7.33 (dd, 1H), 7.10 (t, 1H)].

[Reaction 10]

-continued

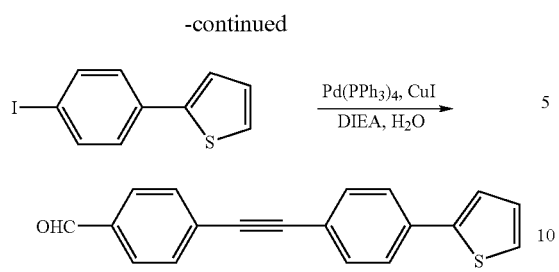

[Reaction 11]

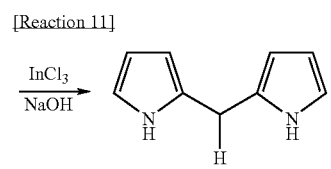

F. Synthesis of Dipyrromethane

As shown in the following Reaction 11, 35 mL (500 mmol, 100 eq) of pyrrole was added to 0.15 g (5 mmol) of formaldehyde at room temperature, and the reaction solution was stirred for 10 minutes under nitrogen atmosphere, and then was again stirred for 10 minutes at temperature of 55° C. Next, 0.11 g (0.5 mmol, 0.1 eq) of indium chloride was added thereto, and the reaction solution was stirred for 150 minutes. After stopping the heating, 0.6 g (15 mmol, 3 eq) of sodium hydroxide was added thereto, and the reaction solution was stirred for 1 hour. Next, the reaction solution was filtered with ether using a funnel charged with celite, and the filtered solution was extracted with organic solvent mixtures (ethylacetate:n-hexane=1:4, volume ratio) 2 times and with 1M sodium chloride aqueous solution 1 time. Next, the organic solvent layer was dehydrated with magnesium sulfate, filtered, and then distilled with reduced pressure. The compound distilled under reduced pressure was purified with a column chromatography (mobile phase volume ratio; ethylacetate:n-hexane=1:10) to obtain 400 mg of dipyrromethane with the yield of 55%. NMR data of the obtained compound is as follows. [$^1$H NMR (400 MHz, CDCl$_3$): δ 7.90 (s, 2H), 6.63 (d, 2H), 6.14 (t, 2H), 6.03 (d, 2H), 3.95 (s, 2H)].

G. Synthesis of Monomer of Compound for Molecular Electronic Devices

As shown in the following Reaction 12, 200 mg (1.39 mmol) of dipyrromethane obtained in F of Example 1-2 and 400 mg (1.39 mmol) of 4-(4-thiophen-phenylethynyl)-benzaldehyde obtained in E of Example 1-2 were melted in 120 mL of chloroform at room temperature, and then the reaction solution was stirred under nitrogen atmosphere for 10 minutes. After stirring, two drops of trifluoroboron diethylether (BF$_3$OEt$_2$) were added thereto, and the reaction solution was again stirred for 3 hours. Next, 315 mg (1.30 mmol) of 2,3-dichloro-5,6-dicyano-p-benzoquinone (DDQ) was added thereto, and the reaction solution was again stirred for 2 hours, and then the solvent was distilled under reduced pressure. The compound distilled under reduced pressure was purified with a column chromatography (mobile phase volume ratio; methylenechloride:n-hexane=1:1) to obtain 35 mg of 5,15-bis(4-thiophendiphenylethynyl)-10,20-bis(phenyl) porphyrin with the yield of 3%. NMR data of the obtained compound is as follows. [$^1$H NMR (400 MHz, CDCl$_3$): δ 10.35 (s, 2H), 9.48 (d, 4H), 9.12 (d, 4H) 8.85 (d, 4H), 8.19 (m, 8H), 7.70 (m, 6H), −2.9 (s, 2H)].

[Reaction 12]

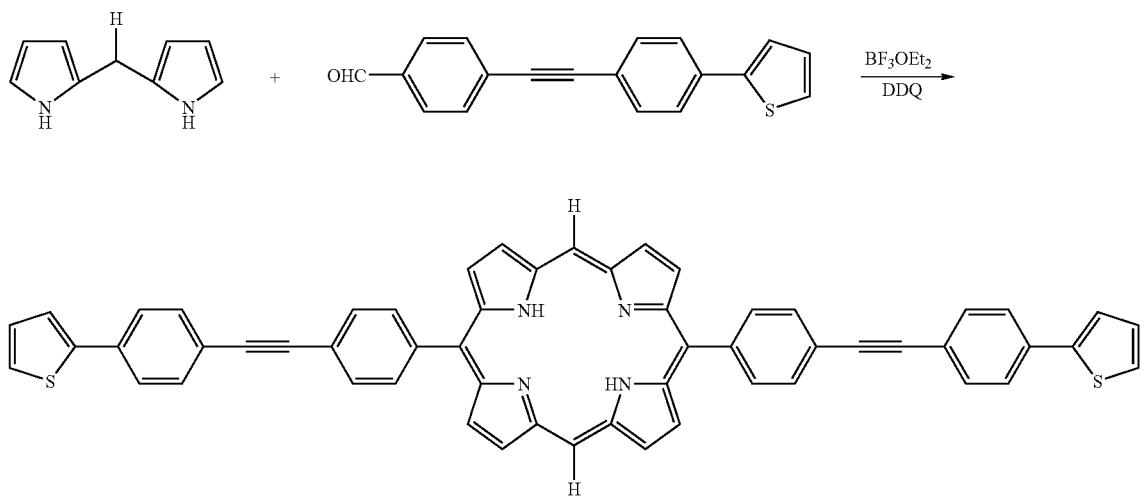

Example 2-1

Production of Compound for Molecular Electronic Device 50 mL of 3,4-ethylenedioxythiophene was added to 1 mg of monomer obtained in Example 1-1, and 0.75 mL of styrene sulfonic acid polymer and 10 mL of water added to form an emulsion, and 0.1 g of ammonium persulfate was added thereto to produce the compound of Formula. 1, wherein the single molecule having an electrical conductivity (R) was

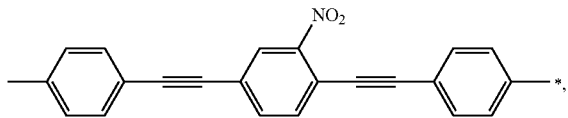

and the repeating unit of polymer parts having an electrical conductivity (M) was

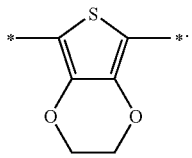

By comparing the viscosity of the obtained compound with the viscosity of polyaniline of a known molecular weight, it is found that the polymerization degree (n) of the polymer parts of the obtained compound was 100 to 500 according to the polymerization condition. Also, the absorbance of the obtained compound was measured with UV-Near IR, and the result is shown in FIG. 3. As shown in FIG. 3, the tail peak of long wavelengths (more than 900 nm), which was generally produced when PEDOT (poly(3,4)ethylenedioxythiophene) was synthesized, was observed. Therefore, the production of polymer having a high electrical conductivity is confirmed.

Example 2-2

Production of Compound for Molecular Electronic Device

Except for using 1.7 mg of the monomer produced in Example 1-2 instead of the monomer produced in Example 1-1, the compound for molecular electronic devices was synthesized in the same manner described in Example 2-1. From the viscosity of the obtained compound, it is found that the polymerization degree (n) of the polymer parts of the obtained compound was 100 to 500.

Example 3-1

Preparation of Molecular Electronic Device 2 mL of isopropyl alcohol was added to 10 mL of aqueous solution, in which 700 mg of the compound for molecular electronic devices obtained in Example 2-1 was dispersed, to obtain an ink composition. An electrode pattern having the width of 1 mm was formed on a plastic film made of PET (polyethylene terephthalate) or PI(polyimide). Then, the ink composition was printed on the electrode pattern, and dried. Next, an additional electrode pattern was formed on the compound layer for molecular electronic devices to obtain a molecular electronic device. FIG. 4 is a photograph of the produced molecular electronic devices.

Example 3-2

Preparation of Molecular Electronic Device

Except for using the compound obtained in Example 2-2 instead of the compound obtained in Example 2-1, the molecular electronic device was produced in the same manner described in Example 3-1.

Test for Negative Differential Resistance (NDR) Characteristics

The Negative Differential Resistance (NDR) characteristics of the produced molecular electronic device was evaluated by applying voltages on the molecular electronic device produced in Example 3-1 while changing the voltages, and measuring the current passing the molecular electronic device. Tests for I (current) vs V (voltage) characteristics were repeated 10 times at room temperature, and a graph of the I (current) vs V (voltage) characteristics is shown in FIG. 5. As shown in FIG. 5, at room temperature, similar NDR results were obtained from the repeated tests. In addition, as shown in FIG. 5, as the voltage increases, the current passing the molecular electronic device initially increases, and then rapidly decreases. Thus, it is confirmed that the molecular electronic device has the NDR characteristics.

Test for Hysteresis Characteristics and Stability

In order to check whether the molecular electronic device produced in Example 3-1 can work as a memory cell, the I-V hysteresis for enabling "write" operation of the molecular electronic device and the reproducibility (stability) of the hysteresis characteristics were evaluated, and the results is shown in FIG. 6. To evaluate the reproducibility and stability of the I-V hysteresis characteristics, I-V scan was carried out with changing the bias voltage from $-5V \rightarrow 0V \rightarrow +5V \rightarrow 0V \rightarrow -5V$, and the scan was repeated for 10 times for the molecular electronic device. The current values measured at the voltage of $-1V$ are shown on the right side graph in FIG. 6. As shown in FIG. 6, if the bias voltage was scanned from $-6V$ to $+6V$, the current changes in the range between about $10^{-3}$A and $10^{-5}$A, and OFF of a low conduction state and ON of a high conduction state were appeared at $-1V$. Accordingly, by changing the bias polarity ($+1V$ and $-1V$), the OFF of a low conduction state and the ON of a high conduction state can be erased. Therefore, by applying pulse of $+1V$ and $-1V$ to the molecular electronic device, Read, Write, and Erase operations can be repeatedly carried out.

Pulse Switching

A write voltage of $+1V$, a read voltage of $+1V$, and an erase voltage of $-1V$ were applied to the molecular electronic device produced in Example 3-1. The Read($+1V$)/Erase($-1V$) voltages were repeatedly applied to the molecular electronic device by 20 times, and the current passing the molecular electronic device was measured, and the results are shown in FIG. 7. As shown in FIG. 7, the current ratio between the ON state and the OFF state was more than $10^4$, and the current ratio was uniformly maintained during the voltage changes of 20 times.

As described above, the compound for molecular electronic devices according to the present invention and the molecular electronic device including the compound were produced by chemically bonding a single molecule having a memory function between polymers having an electrical conductivity. Therefore, the compound and the molecular electronic device can prevent the electrical short between electrodes, and can be produced economically and efficiently. In addition, according to the present invention, the NDR characteristics can be obtained with the devices having the small size of several hundred micrometers.

The invention claimed is:

1. A compound for molecular electronic device having the structure of following Formula 1,

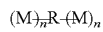 <Formula 1> wherein,

R is formed from a single molecule having an electrical conductivity, and has the following Formula 2, or has the following structure

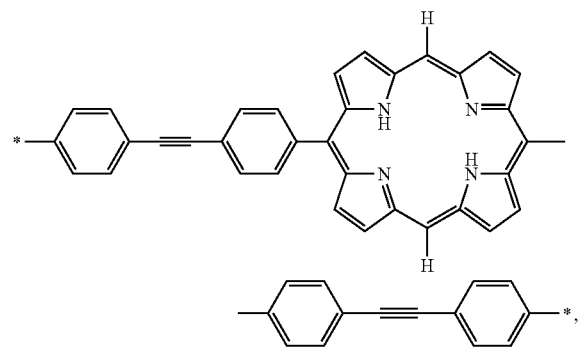

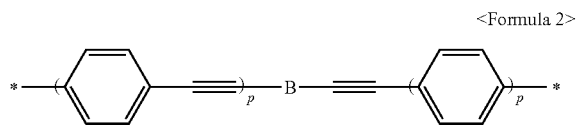

M is independently a repeating unit constituting a polymer having an electrical conductivity, and n is independently an integer ranging from 100 to 500, <Formula 2> wherein, p is independently an integer from 1 to 3, and B is a substituted or non-substituted ring structure compound with 4-30 carbon atoms in which a double bond and a single bond are alternately repeated.

2. A compound for molecular electronic device having the structure of following Formula 1,

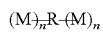 <Formula 1> wherein, R is

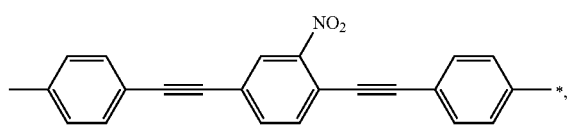

n is independently an integer ranging from 100 to 500, and M is

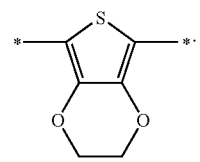

3. The compound for molecular electronic device according to claim 1, wherein the B is a phenyl group or a pyridine group substituted with an amino group or nitro group.

4. The compound for molecular electronic device according to claim

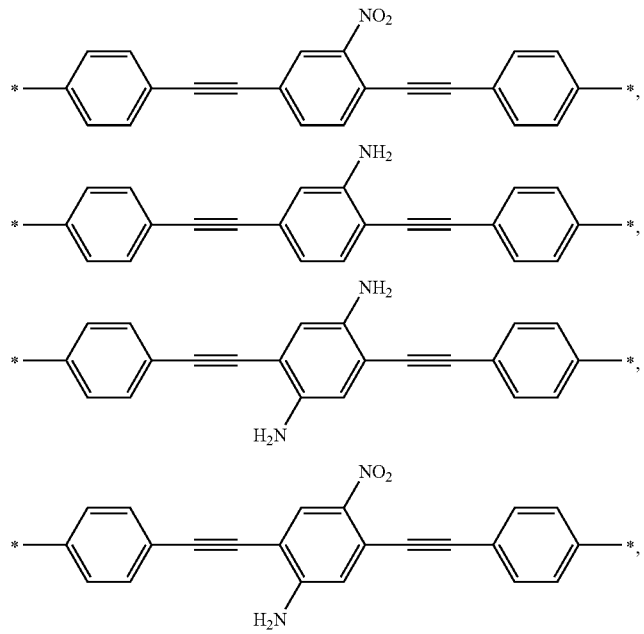

-continued

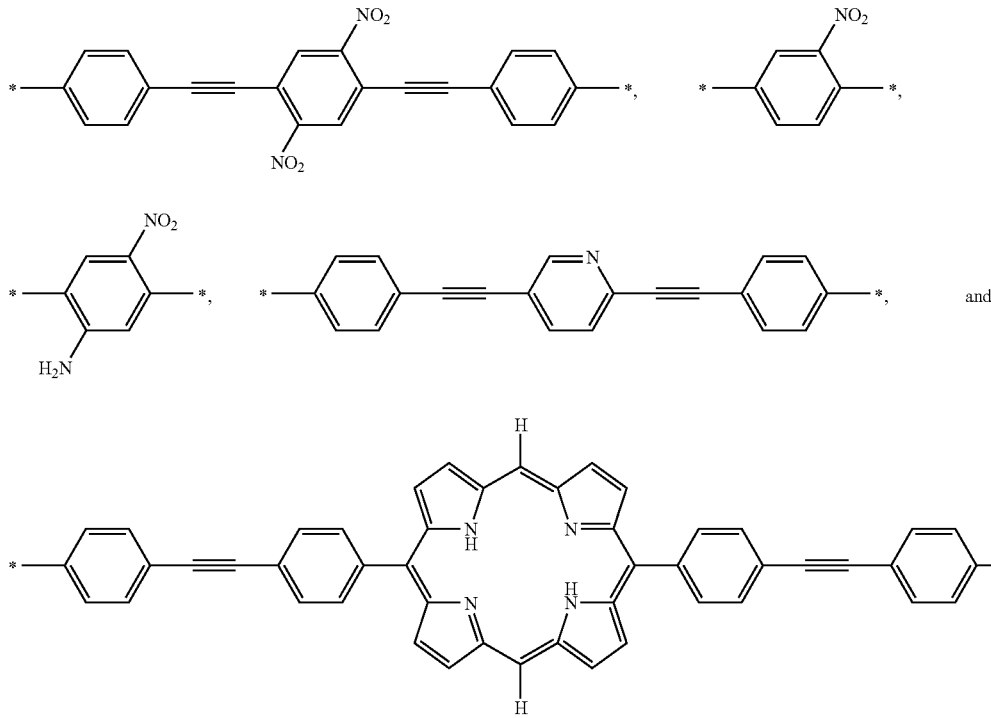

5. The compound for molecular electronic device according to claim 1,

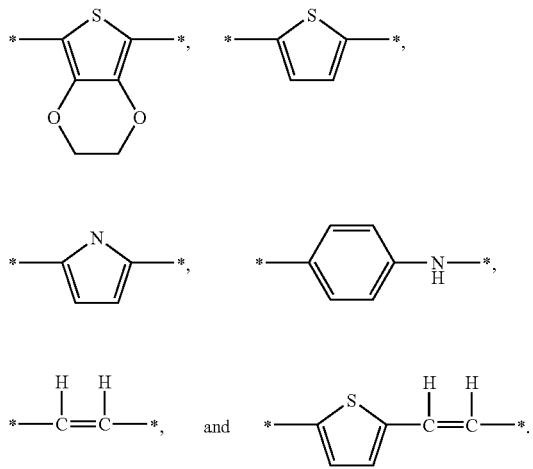

6. A molecular electronic device including the compound having the structure of following Formula 1,

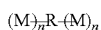 <Formula 1> wherein, R is formed from a single molecule having an electrical conductivity, and has the following Formula 2, M is independently a repeating unit constituting a polymer having an electrical conductivity, and n is independently an integer ranging from 100 to 500,

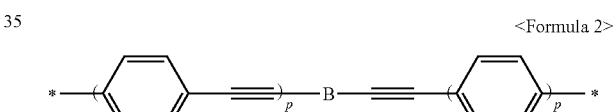 <Formula 2> wherein, p is independently an integer from 1 to 3, and B is a substituted or non-substituted ring structure compound with 4-30 carbon atoms in which a double bond and a single bond are alternately repeated.

7. The molecular electronic device according to claim 6, wherein the electronic device includes the compound of Formula 1; and a pair of opposing electrodes on which the polymer parts of the compound of Formula 1 are respectively coated.

8. The molecular electronic device according to claim 6, wherein the molecular electronic device is selected from the group consisting of a molecular memory, a molecular switch, a molecular rectifier, and a molecular wire.

9. A method for producing a molecular electronic device comprising the steps of:
patterning a lower electrode on a substrate;
coating an ink, in which the compound having the structure of Formula 1 is dissolved in a solvent, on the lower electrode and then removing the solvent; and
forming an upper electrode on the compound having the structure of Formula 1,

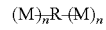 <Formula 1> wherein,
R is formed from a single molecule having an electrical conductivity, and has the following Formula 2, or has the following structure

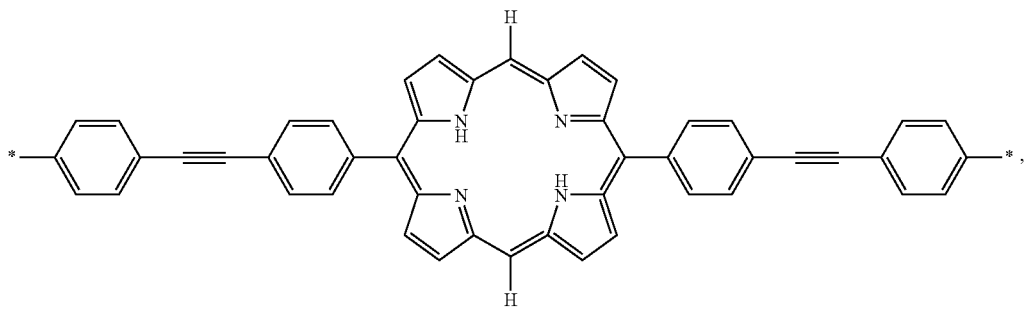

M is independently a repeating unit constituting a polymer having an electrical conductivity, and n is independently an integer ranging from 100 to 500, <Formula 2>

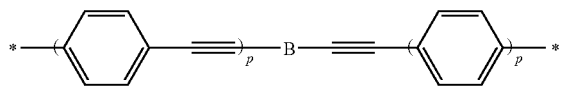

wherein, p is independently an integer from 1 to 3, and B is a substituted or non-substituted ring structure compound with 4-30 carbon atoms in which a double bond and a single bond are alternately repeated.

10. The compound for molecular electronic device according to claim 1, wherein the B is a substituted or non-substituted ring structure compound with 5-30 carbon atoms or wherein R is

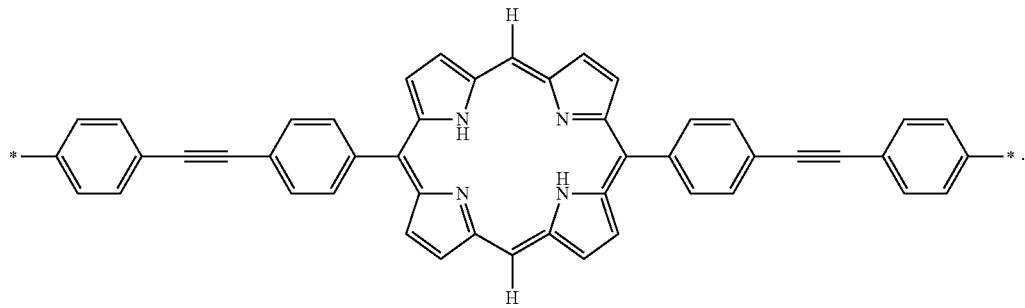

11. The compound for molecular electronic device according to claim 1, wherein the B is a phenyl or pyridine ring or wherein R is

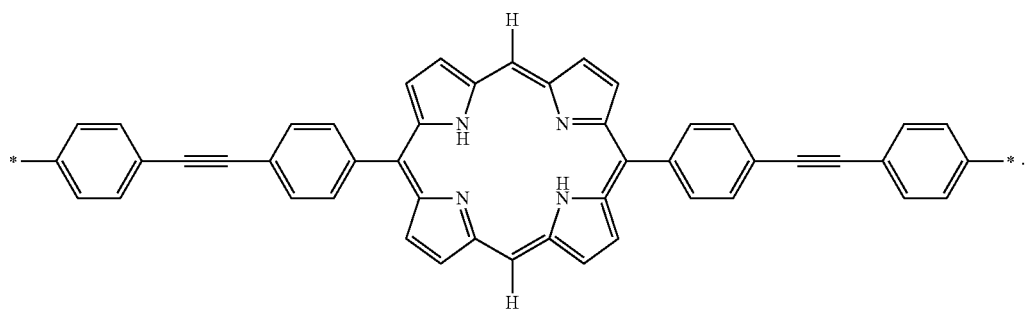

* * * * *